(12) United States Patent
Egle et al.

(10) Patent No.: US 7,678,088 B2
(45) Date of Patent: Mar. 16, 2010

(54) PORTKATHETER

(75) Inventors: Walter Egle, Koblach (AT); Martin Hohlrieder, Götzis (AT)

(73) Assignee: A.M.I. Agency for Medical Innovations GmbH, Feldkirch (AT)

( * ) Notice: Subject to any disclaimer, the term of this patent is extended or adjusted under 35 U.S.C. 154(b) by 0 days.

(21) Appl. No.: 12/153,992

(22) Filed: May 28, 2008

(65) Prior Publication Data
US 2009/0259187 A1    Oct. 15, 2009

(30) Foreign Application Priority Data
Apr. 15, 2008   (AT)   ............................ GM 219/2008

(51) Int. Cl.
*A61M 37/00*   (2006.01)
(52) U.S. Cl. .............................. 604/288.01; 604/288.02
(58) Field of Classification Search ................................
604/288.01–288.04, 891.1, 167.01–167.04, 604/201
See application file for complete search history.

(56) References Cited

U.S. PATENT DOCUMENTS

| | | | | |
|---|---|---|---|---|
| 3,995,628 | A * | 12/1976 | Gula et al. ................... | 604/159 |
| 4,721,123 | A * | 1/1988 | Cosentino et al. ......... | 134/57 R |
| 4,751,926 | A | 6/1988 | Sasaki | |
| 5,919,160 | A | 7/1999 | Sanfilippo, II | |
| 6,074,377 | A | 6/2000 | Sanfilippo, II | |
| 6,210,366 | B1 | 4/2001 | Sanfilippo, II | |
| 6,258,058 | B1 | 7/2001 | Sanfilippo, II | |
| 6,575,891 | B1 * | 6/2003 | Castelo et al. ................. | 600/7 |
| 6,613,013 | B2 * | 9/2003 | Haarala et al. ............ | 604/93.01 |
| 7,445,614 | B2 * | 11/2008 | Bunodiere et al. ..... | 604/288.02 |
| 2004/0055628 | A1 * | 3/2004 | Yu ............................. | 135/20.1 |
| 2004/0204692 | A1 * | 10/2004 | Eliasen .................. | 604/288.02 |
| 2005/0004526 | A1 | 1/2005 | Reinemann | |
| 2006/0178647 | A1 * | 8/2006 | Stats .................... | 604/288.01 |
| 2006/0217668 | A1 | 9/2006 | Schulze et al. | |

(Continued)

FOREIGN PATENT DOCUMENTS

DE   84 37 873   5/1986

(Continued)

OTHER PUBLICATIONS

Austrian Search Report issued Sep. 25, 2008 in the corresponding Austrian patent application.

(Continued)

*Primary Examiner*—Kevin C Sirmons
*Assistant Examiner*—Edelmira Bosques
(74) *Attorney, Agent, or Firm*—Wenderoth, Lind & Ponack L.L.P.

(57) ABSTRACT

A port catheter for introducing a fluid into a hollow organ of a human or animal body includes a port unit implantable into the human or animal body, which port unit includes an interior chamber, to which the fluid to be introduced into the hollow organ of the human or animal body can be supplied. The port catheter further includes a tube connected to the port unit, which tube includes an inner channel through which fluid can be conducted into the hollow organ. The port catheter further includes a grip piece connected to the port unit and removable from it, for the manipulation of the port unit during the implantation of the port catheter into the human or animal body.

9 Claims, 4 Drawing Sheets

U.S. PATENT DOCUMENTS

| | | |
|---|---|---|
| 2006/0293627 A1 | 12/2006 | Byrum et al. |
| 2007/0073250 A1* | 3/2007 | Schneiter ............... 604/288.01 |
| 2008/0058595 A1* | 3/2008 | Snoke et al. ................ 600/114 |
| 2008/0319399 A1* | 12/2008 | Schweikert et al. ......... 604/175 |

FOREIGN PATENT DOCUMENTS

| | | |
|---|---|---|
| DE | 201 14 795 | 3/2002 |
| EP | 0260080 A2 | 3/1988 |
| EP | 1736195 A1 | 12/2006 |

OTHER PUBLICATIONS

European Search Report (with English translation of first page) issued Jul. 21, 2009 in International (PCT) Application No. EP 09005140.

* cited by examiner

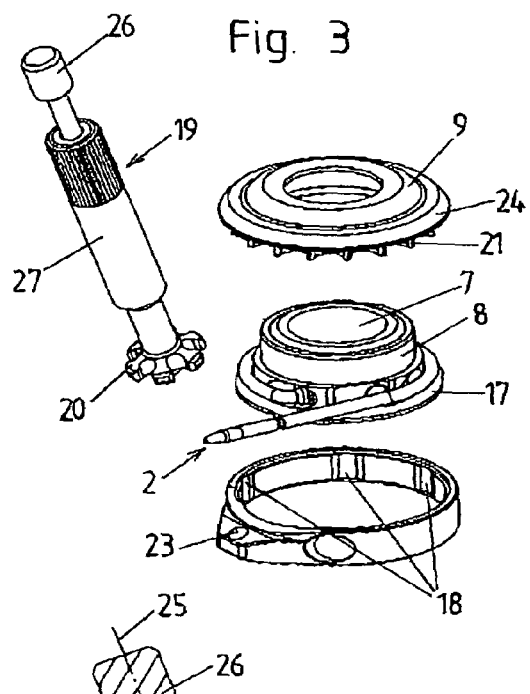
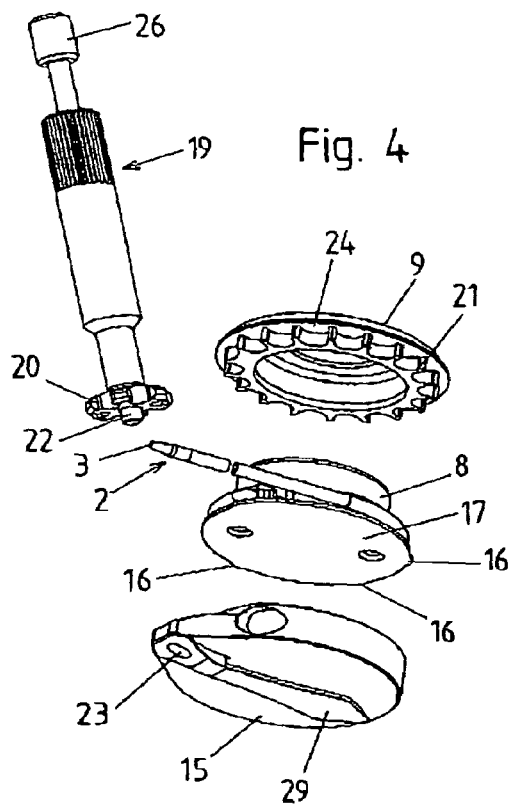
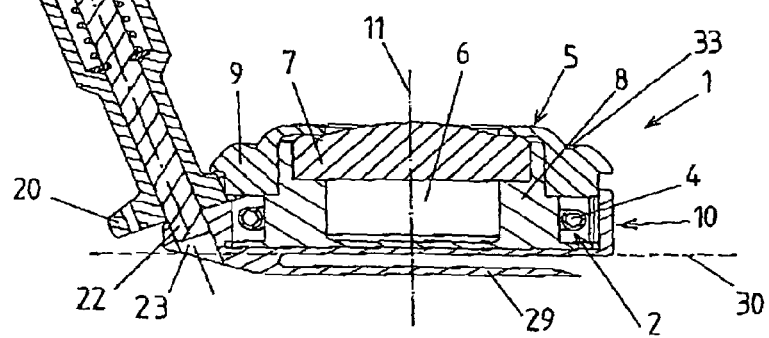

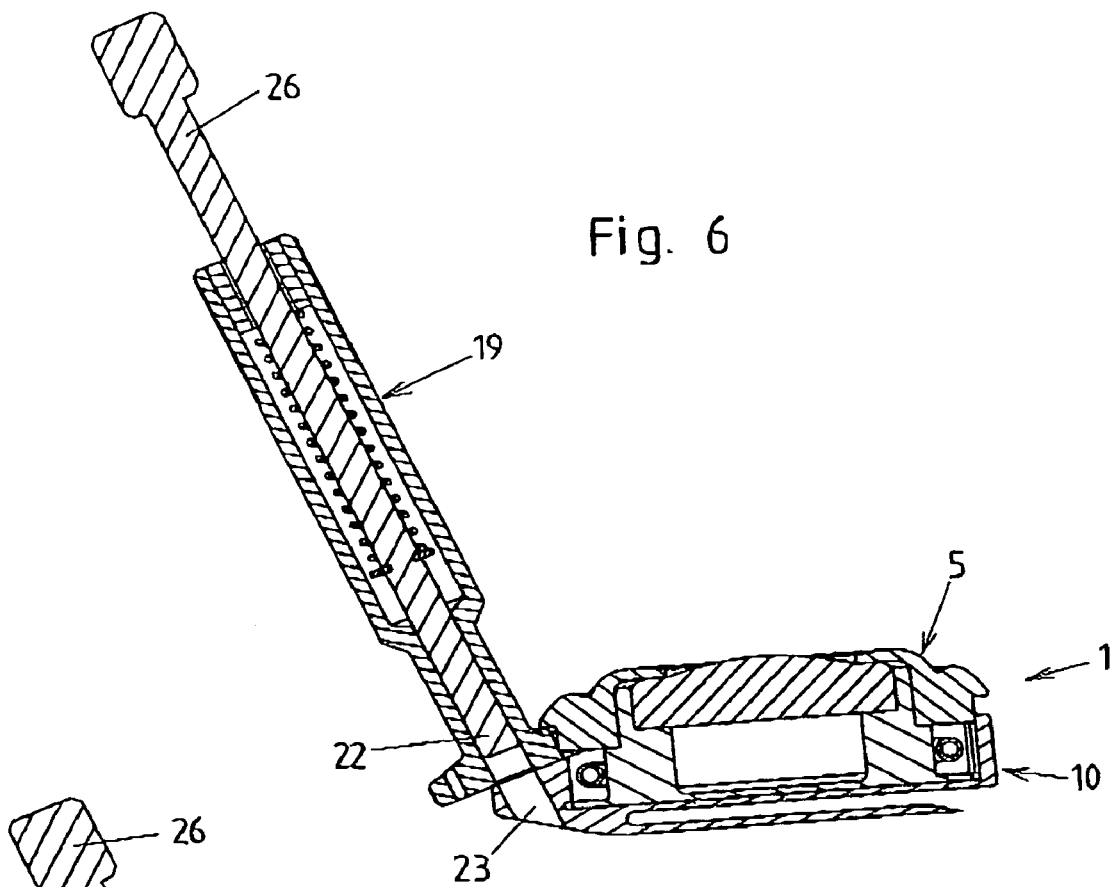
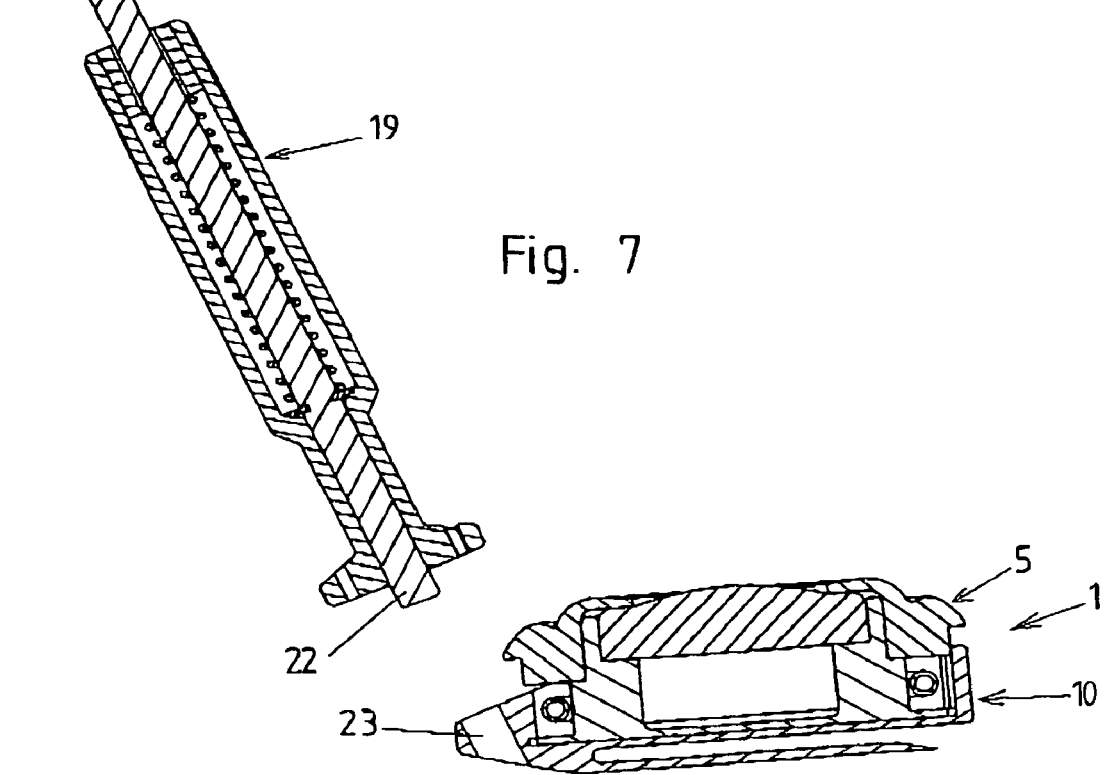

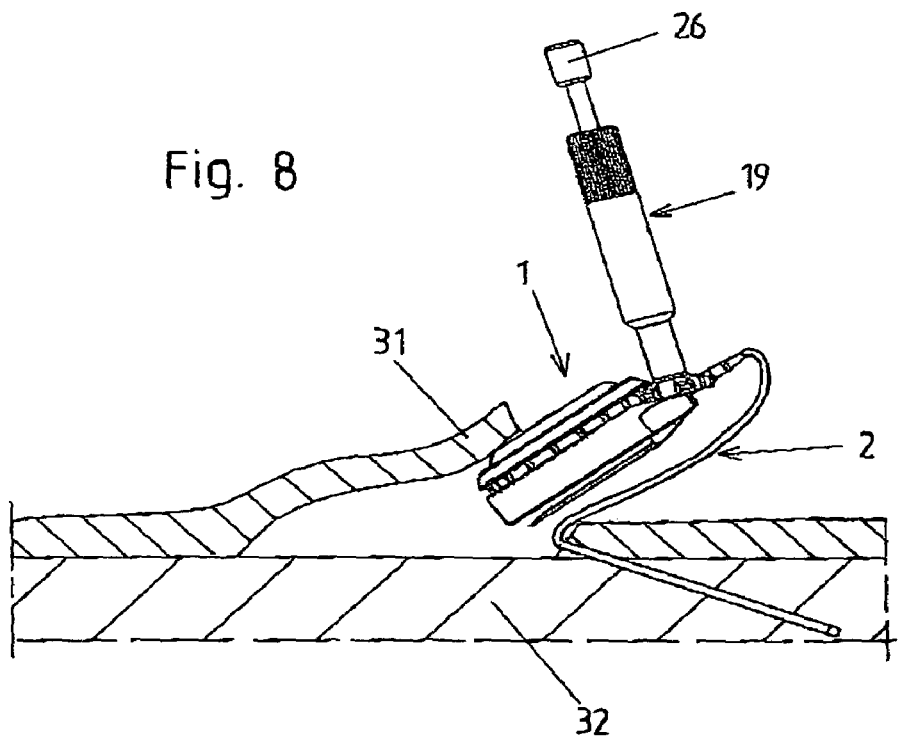
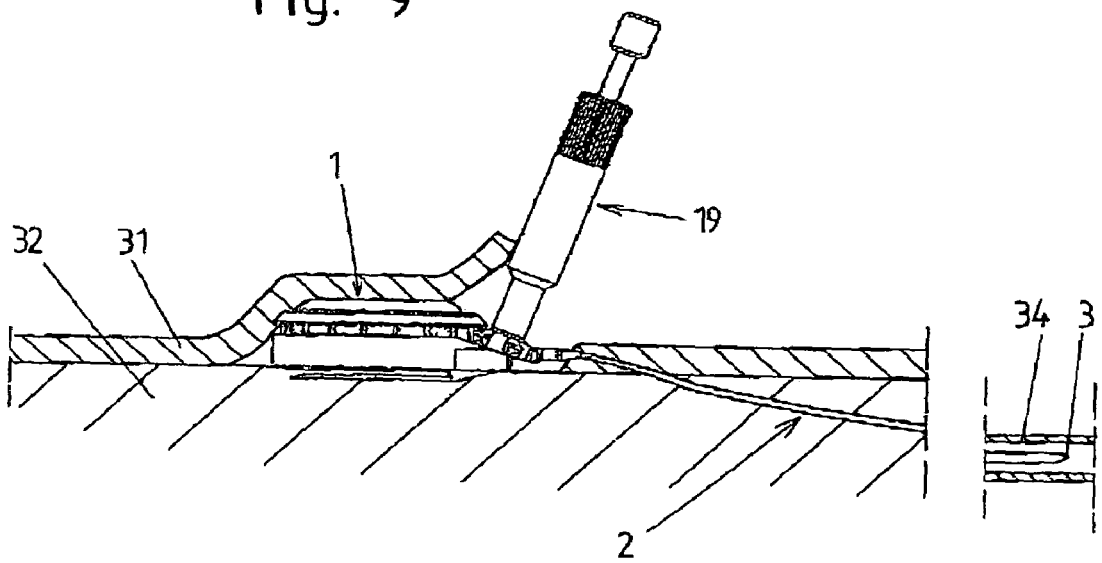

PORTKATHETER

BACKGROUND OF THE INVENTION a) Field of the Invention

The invention relates to a port catheter for introducing a fluid into a hollow organ of a human or animal body, with a port unit implantable into the human or animal body, which port unit includes an interior chamber, to which can be supplied the fluid to be introduced into the hollow organ of the human or animal body, and a tube connected to the port unit, which tube comprises an inner channel through which the fluid can be conducted into the hollow organ.

b) Description of Related Prior Art

Port catheters serve for introducing fluids, for example for drug therapy, into hollow organs of the human or animal body. In this way, for example in chemotherapy, drugs are introduced directly into the blood circulation. Apart from the introduction of fluids into blood vessels, fluids can also be introduced using port catheters into the gastrointestinal tract, the bladder and other hollow organs.

Port catheters conventionally have a cup-shaped port unit with a chamber closed by a silicon diaphragm and a tube connected to the port unit. By piercing the silicon diaphragm the fluid to be introduced into the hollow organ is injected into the chamber of the port unit and reaches the hollow organ through the inner channel of the tube disposed with its delivery end in the hollow organ. The port unit is conventionally implanted subcutaneously.

A conventional surgical procedure for implanting the port catheter is the Seldinger technique. In this technique a needle with a sleeve disposed thereon is advanced into the hollow organ, in particular the blood vessel. After the inner needle has been pulled out, the tube with its delivery end directed ahead can be slid through the sleeve into the hollow organ until the delivery end has reached the desired site. The sleeve is subsequently removed. For this purpose the sleeve can be torn open longitudinally along a tear line and consequently can be separated from the tube. The tube is subsequently brought to the desired length and placed onto a connection piece of the port unit. The port unit is inserted into the prepared skin pocket and fixed in position on the fascia by suturing.

A disadvantageous step in this surgical procedure is the shortening of the tube to the correct length and the subsequent joining together with the connection piece of the port unit. During this joining no air bubbles are allowed to enter the tube. The delivery end of the tube in the hollow organ must, as much as possible, not become displaced. In addition, the shortening of the tube and the joining together of the shortened tube with the connection piece requires intensive manipulation of the parts of the port catheter. Each contact of the port catheter by the surgeon or each contact of the port catheter with the skin of the patient more or less impairs the sterility of the port catheter, which entails a corresponding infection risk through the implanted port catheter.

DE 8 437 873 U1 discloses a port catheter in which the length of the tube connecting to the port unit is implemented such that it is variable. For this purpose the tube can be partially disposed in the cup-shaped port unit and be drawn out of the connection piece of the port unit to the desired length. In another embodiment the tube is wound about a reel rotatably disposed in a port housing and can be pulled out of the port housing in the desired length. While through this implementation a simplification of the required manipulation during the surgery can be attained, through the required manipulation on the port catheter there yet is the risk of impairing the sterility.

SUMMARY OF THE INVENTION

The invention addresses the problem of improving the sterility of a port catheter in the implantation. This is solved according to the invention through a port catheter for introducing a fluid into a hollow organ of a human or animal body, comprising a port unit implantable into the human or animal body. The port unit includes an interior chamber to which can be supplied the fluid to be introduced into the hollow organ of the human or animal body. The port catheter also comprises a tube connected to the port unit and the tube has an inner channel through which the fluid can be conducted into the hollow organ. A grip piece is connected with the port unit and removable from it for manipulating the port unit during the implantation of the port catheter into the human or animal body.

In implanting the port catheter, the port unit can thus be held by the grip piece connected with it such that the requirement to contact the port unit itself is decreased or avoided. After inserting the port unit at the prepared site in the body, the grip piece can be removed. The grip piece can thus be separated from the port unit without destruction and preferably without tools, for example by means of a movable actuation element of the grip piece, via which at least one connecting element of the grip piece is movable with which this connecting element engages into an engagement element of the port unit. In a feasible embodiment, this actuation element can be an element displaceable with respect to a grip component of the grip piece, by means of which the at least one connecting element can be pulled, for example, out of the associated engagement element. Actuation elements swivelable or rotatable with respect to a grip component can also be provided. A detachable coupling of the grip piece with the port unit can be implemented in several forms.

The length of the tube projecting from the port unit is preferably variable, and it is especially preferred if the projecting length of the tube is variable by means of the grip piece connected with the port unit, for example by rotation of the grip piece or a component of the grip piece about the longitudinal axis of the grip piece.

In an advantageous embodiment of the invention the port unit comprises a cup which includes the interior chamber for receiving the fluid to be introduced into the hollow organ of the human or animal body, and a base part with respect to which the cup is rotatable for varying the length of the tube projecting from the port unit. To vary the length of the tube projecting from the port unit, the cup is rotated with respect to the base part. Thereby a section of the tube of greater or lesser length, which tube connects the connection end of the tube connected with the port unit, extends about a circumferential segment of the cup and the projecting length of the tube varies accordingly.

Such an implementation of the port catheter allows an advantageous surgical procedure in which the tube already attached to the cup is introduced with its delivery end directed forwardly into the hollow organ (for example according to the Seldinger technique). Furthermore, the port unit held on the grip piece is inserted by means of the grip piece into the prepared site, in particular into a skin pocket, of the human or animal body. Before or after, or before as well as also after, insertion of the port unit, the free length of the tube can be adapted by rotating the cup with respect to the base part. This adaptation can here include in particular a shortening of the free length of the tube. The adaptation, in particular shortening, of the free length of the tube can take place by means of the grip piece, in particular by rotating the grip piece or a component of the grip piece about the axis of the grip piece.

For rotating the cup with respect to the base part, the grip piece advantageously comprises a gearing member cooperating with a gearing member of the cup. An advantageous embodiment provides cooperating gearing members in the form of toothed wheels or pinion gears.

A preferred procedure for the implantation of the port catheter provides that the delivery end of the tube is initially introduced somewhat further into the hollow organ than its intended final position. After placing the port unit at the prepared site of the human or animal body, the tube can again be pulled back slightly by rotating the cup with respect to the base part, while shortening the free length of the tube, until the delivery end is located at the intended site. The shortening of the free length of the tube can here take place by means of the grip piece as well as insertion of the port unit into the intended site in the body. Pulling back the tube can also be carried out under X-ray control, such that an exact placement of the delivery end is attained. The grip is subsequently removed from the port unit and the opening in the body, through which the port unit had been introduced, is closed. The entire implantation of the port catheter can in this manner be completed by the surgeon without direct contact of the port unit by the surgeon and preferably also without direct contact of the tube (which can be guided with an appropriate instrument).

Before the implantation the entire port catheter can advantageously be already filled with fluid, for example sterile saline solution. The occurrence of air bubbles can thereby be effectively avoided.

To secure the port unit on the tissue of the human or animal body, the base part can advantageously comprise at least one securement element that can be inserted into the tissue. This securement on the tissue can conveniently also form a counterbearing for the rotation of the cup with respect to the base part by means of the grip piece.

It is preferred if the tube is already connected at the factory, and thus in the delivery condition, with the cup. It can herein conveniently have its greatest possible free length and, starting from this state, can be retractable more or less far into the port unit.

In conjunction with the enclosed drawings further advantages and details of the invention will be described in the following.

DESCRIPTION OF THE PREFERRED EMBODIMENTS

Figure 1:
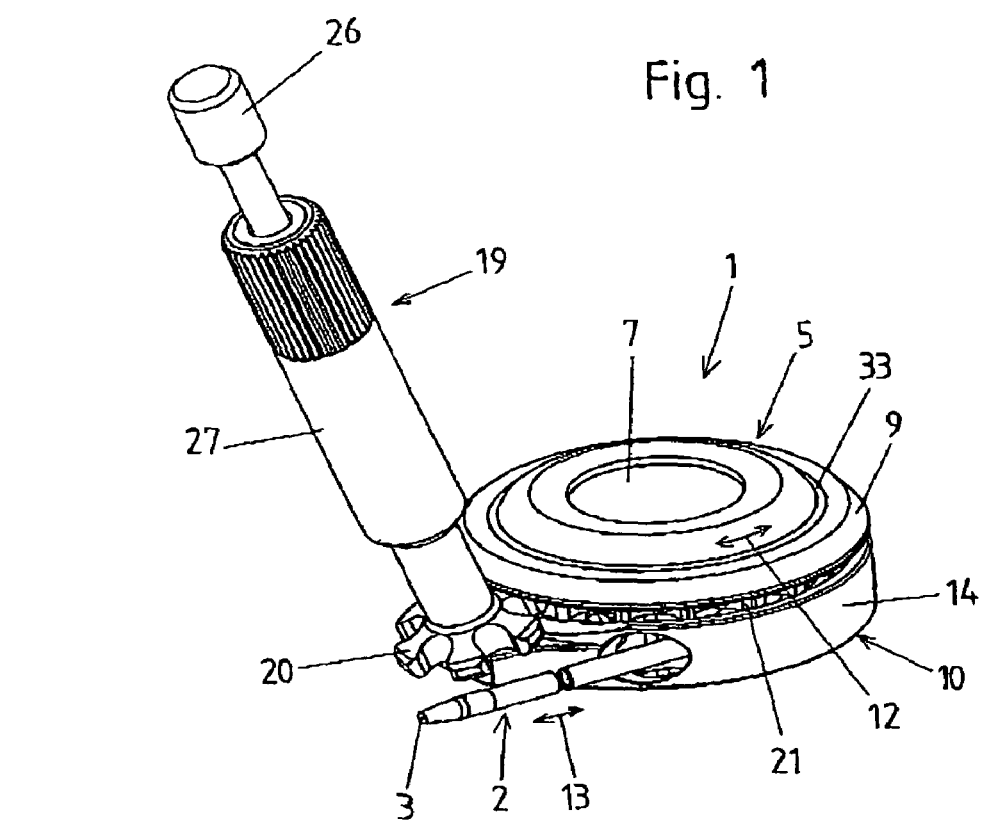
FIG. 1 an oblique view of a port catheter according to the invention, the tube only being drawn over a portion of its length and a grip piece being attached on the port unit, FIG. 2 an oblique view according to FIG. 1 from a different viewing direction, FIGS. 3 and 4 oblique views of the port catheter from different viewing directions, representation of the parts of the port catheter taken apart in the manner of an exploded view, FIG. 5 a longitudinal central section through the port catheter with attached grip piece, FIG. 6 a section corresponding to FIG. 5, however the connecting element of the grip piece being retracted, FIG. 7 a longitudinal section corresponding to FIG. 5, however with the grip piece having been removed from the port unit, FIGS. 8 and 9 schematic representations to illustrate the implantation of the port catheter.
Figure 2:
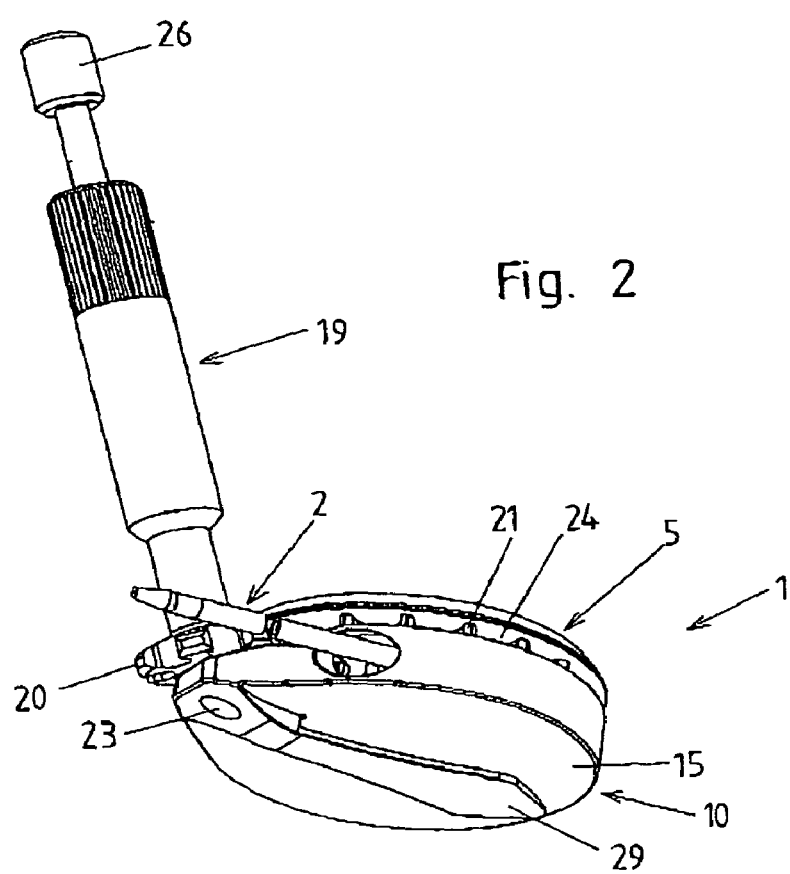

An embodiment of a port catheter according to the invention, which can also be referred to as an infusion port, is shown in the Figures. The port catheter comprises a port unit 1 and a catheter tube 2 connected with a connection end on the port unit 1. At its delivery end 3 opposite its connection end, a fluid flowing through the inner channel 4 of the tube 2 can be introduced into a hollow organ of a human or animal body after the port catheter has been implanted into the human or animal body.

The port unit 1 includes a cup 5 with an interior chamber 6 into which the fluid to be introduced into the hollow organ is to be placed. For this purpose, a diaphragm 7 delimiting a section of the interior chamber 6 can be pierced by an injection needle in order to inject the fluid into the chamber 6. After the injection needle is withdrawn, the puncture opening of diaphragm 7 closes again due to the elasticity of the material of diaphragm 7, which can be comprised, in particular, of silicon.

In the depicted embodiment example the diaphragm 7 is set in between a lower cup part 8 and a upper cup part 9, the upper cup part 9 having an opening through which the diaphragm 7 is accessible.

The inner channel 4 of tube 2 communicates with chamber 6 of cup 5. The tube 2 is, for example, placed with its connection end onto a connecting piece of cup 5, which includes a bore opening out into chamber 6.

The port unit 1 further includes a base part 10. With respect to the base part 10, the cup 5 is rotatable about an axis of rotation 11 (see FIG. 5). Thereby the length of tube 2 projecting from cup 5 or from the port unit 1 can be varied. For this purpose a section of tube 2 adjoining the connection end is guided about a circumferential segment of cup 5. Through rotation of the cup 5 with respect to base part 10, this circumferential segment of cup 5 about which the tube extends around the cup 5, and consequently, also the free length of tube 2, can be varied. The possible rotational directions of cup 5 relative to base part 10 are symbolized in FIG. 1 by a double arrow 12, and the associated movement of the tube is indicated by a double arrow 13.

Base part 10 includes an annular section 14 with which it encompasses the outer annular contact section of cup 5 for tube 2. In the annular section 14 is formed a passage opening for tube 2 through which the tube exits from the port unit 1.

In the depicted embodiment example, the base part 10 furthermore has a bottom 15, from which projects the annular section 14. Such a bottom could also be omitted.

The base part 10 supports the cup 5 such that it is rotatable about the rotational axis 11. In the depicted embodiment in the rotational position of cup 5 in which the tube 2 is wound furthest onto cup 5, noses 16 could be slid in on a bottom plate 17 of the lower cup part 15 of base part 10 along trench-shaped indentations 18 of annular section 14 up to the bottom 15 of the base part 10. The noses 16 reach into a circumferential groove at the lower end of the annular section 14, which groove makes possible the rotation of cup 5 relative to base part 10 and extending the free length of the tube. After the initial rotation of cup 5 relative to the annular section 14, a snap part can be passed over, which, during a subsequent back-rotation of the cup 5, acts as a stop which brings about that the cup 5 can no longer be rotated back so far that the noses 16 reach into the associated indentations 18. This prevents the cup 5 from being pulled out of the base part 10.

For the manipulation of the port unit 1 during the implantation of the port catheter into the human or animal body an elongated grip piece 19 is provided. During the implantation of the port catheter this grip piece is coupled to the port unit 1 and projects from it, as is evident in FIGS. 1, 2, 5, 8 and 9.

The grip piece 19 includes a toothed wheel 20 which meshes with a toothed wheel 21 disposed on cup 5. In the depicted embodiment example, the toothed wheel 21 is herein implemented in one piece with the upper cup part 9. Other implementations are also conceivable and feasible, for example the development on the lower cup part 8 or in the form of a separate part held on the upper cup part 9 and/or lower cup part 8.

To connect the grip piece 19 with the port unit 1, a connecting element 22 of the grip piece 19 is provided, which engages into an engagement element 23 of the base part 10. In the depicted embodiment the connecting element is formed by a pin-shaped part, which engages into the engagement element 23 formed by a hole. The connecting element 22 projects beneath the toothed wheel 20 beyond the latter and above the toothed wheel 21 is formed an annular collar 24 (in the depicted embodiment example on the upper cup part), on which the toothed wheel 20 is stayed.

The port unit 1 is held in this manner on this grip piece in the state coupled with the grip piece 10.

In this coupled state, furthermore, through rotation of the grip piece 19 about its longitudinal axis 25 the cup 5 is rotatable relative to the base part 10 if the base part 10 is prevented from rotations about the longitudinal axis 25 (in particular, it is secured in position on the tissue of the human or animal body).

For the removal of the grip piece 19 from the port unit 1, the grip piece 19 has an actuation element 26 by means of which the connecting element 22 is retractable in order to be pulled out of the engagement element 23. In the depicted embodiment example the actuation element 26 is formed by a rear end section of a bolt which penetrates a grip component 27 of grip piece 19 and is displaceable relative to this grip piece. The front end section of this bolt forms the connecting element 22. By means of a spring 28 the bolt is spring-loaded in that position in which the connecting element 22 projects beyond the toothed wheel 20.

Detachable couplings for the connection of the grip piece 19 with the port unit 1 can be implemented in various distinct ways.

It would also be conceivable and feasible that only a component of the grip piece is rotated for rotating the cup. This component of the grip piece would be supported rotatably relative to the grip component 27 (it could, for example, be formed about the section of the grip component which is shown as a knurled section in the Figures, which in this case would have to be implemented as a separate rotatable part) and connected torsion-tight with the toothed wheel 20 or another gearing member for rotating the cup 5. The grip component 27 could in this case be nonrotable relative to the base part 10 (for example through a polygonal implementation of the connecting element 22 and of the opening forming the engagement element 23 and a securement against turning out of position of the connecting element 22 relative to the grip component 27).

Instead of cooperating toothed wheels 20, 21, other types of cooperating gearing members, for example cooperating friction wheels, of the grip piece 19 and cup 5 could be provided for rotating the cup 5 relative to the base part 10 by means of the grip piece 19.

For securement on the tissue of the human or animal body, the base part 10 comprises a securement element 29 which can be inserted into the tissue. The securement element 29 is here formed as a blade-shaped part (clip) which can be inserted in a straight line into the tissue. Securement elements implemented in different form, for example securement elements implemented in the shape of a hook, are conceivable and feasible. More than one such securement element can also be provided on the base part. It would, in principle, also be conceivable and feasible that the base part 10 has eyes for suturing the base part to the tissue.

The base part 10 can thus be secured in a contact plane 30 on the tissue. The rotational axis 11 of the cup 5 with respect to the base part 10 is preferably oriented at right angles to the contact plane 30.

Port unit 1 includes a trench-shaped indentation 33 spaced apart from the opening exposing the diaphragm 7, which indentation encompasses this opening. Thereby a safeguard against the injection needle slipping off is formed should the treating physician wishing to inject fluid into the port unit miss the opening exposing the diaphragm 7. This indentation 33 is here disposed in the upper cup part 9. Disposition in the (appropriately drawn high) lower cup part 8 or between the upper cup part 9 and the lower cup part 8 is conceivable and feasible. Instead of a single indentation 33 completely or at least largely encompassing the opening, several indentations encompassing the overall opening at least to a large extent can also be provided.

The port unit is conventionally implanted into a formed skin pocket. This implantation is depicted schematically in FIGS. 8 and 9. In FIG. 8 tube 2 is already inserted through the tissue of the human or animal body into the desired hollow organ, for example a vena cava, following, for example, the Seldinger technique, and a skin layer (with subcutaneous fat tissue) is already cut open. The surgeon lifts the skin pocket with forceps and slides the port unit 1 into this pocket, wherein the securement element 29 is pushed into the fascia underneath the skin 31. These manipulations of the port unit 1 can be carried out when the surgeon holds the grip piece 19 and with it guides the port unit 1 attached on the grip piece 19. Tube 2 is subsequently shortened by rotating the cup 5 by means of the grip piece 19 until the state depicted in FIG. 9 is reached. Herein, the tube 2 is also preferably again pulled for some distance from the tissue until the delivery end 3 has reached the intended site in the hollow organ.

The grip piece 19 is subsequently removed from the port unit 1 by actuating the actuation element 26 and the skin pocket is closed using a suture. The implantation of the port catheter in this manner has been completed without contact of the port unit 1 by the gloves of the surgeon and preferably also without contact of the tube 2 by the gloves of the surgeon.

Although the rotation of the cup 5 relative to the base part 10 for the adaptation of the length of the tube 2 can preferably be carried out by means of the grip piece 19, it would also be conceivable and feasible that this rotation is carried out manually, thus, not taking place through the grip piece 19. For the rotation of the cup 5 herein the surgeon could grasp (manually or with an appropriate instrument) the cup 5 on a section projecting from the base part 10 and rotate it. The cup 5 could also include a tool lug for the rotation tool.

In such examples, the required manipulations through the grip piece 19 in connection with the variability of the length of tube 2 would also be significantly simplified and the requisite contacting of the port unit 1 could be decreased (in the rotation of cup 5 by grasping the cup 5) or be avoided (in utilizing a tool).

As is evident based on the above description, the scope of the invention is not limited to the depicted examples, but rather should be determined with reference to the attached claims together with their full range of feasible equivalents. While the preceding description and the drawing represent the invention, it is obvious to a person of skill in the art that various modifications can be carried out therein without leaving the true spirit and scope of the invention.

LEGEND FOR THE REFERENCE NUMBERS

1 Port unit
2 Tube
3 Delivery end
4 Inner channel
5 Cup
6 Interior chamber
7 Diaphragm
8 Lower cup part
9 Upper cup part
10 Base part
11 Rotational axis
12 Double arrow
13 Double arrow
14 Annular section
15 Bottom
16 Nose
17 Bottom plate
18 Indentation
19 Grip piece
20 Toothed wheel
21 Toothed wheel
22 Connecting element
23 Engagement element
24 Annular collar
25 Longitudinal axis
26 Actuation element
27 Grip component
28 Spring
29 Securement element
30 Contact plane
31 Skin
32 Fascia
33 Indentation

The invention claimed is:

1. A port catheter for introducing a fluid into a hollow organ of a human or animal body, comprising:
a port unit implantable into the human or animal body, and including an interior chamber configured to house the fluid to be introduced into the hollow organ of the human or animal body;
a flexible tube connected to said port unit, said flexible tube having a variable length and including an inner channel configured to conduct the fluid into the hollow organ; and
a grip piece connected to said port unit and removable from said port unit for manipulation of said port unit during implantation of said port catheter into the human or animal body,
wherein, when said grip piece is connected said port unit, such connection enables variation of the length of said flexible tube,
wherein said grip piece is configured to enable variation of the length of said flexible tube by rotation of at least a portion of said grip piece about a longitudinal axis of said grip piece,
wherein said port unit includes a cup including said interior chamber, and a base part, said cup being rotatable with respect to said base part for varying the length of said flexible tube, and
wherein said grip piece includes a gearing member cooperating with a gearing member of said cup.

2. The port catheter as claimed in claim 1, wherein said cooperating gearing member is a toothed wheel.

3. The port catheter as claimed in claim 1, wherein said base part includes an annular section which encompasses said cup.

4. The port catheter as claimed in claim 1, wherein said grip piece includes at least one connecting element, and when said grip piece is connected to said port unit, said at least one connecting element engages an engagement element of said base part.

5. The port catheter as claimed in claim 4, wherein said grip piece includes an actuation element for moving the at least one connecting element of said grip piece for the removal of said grip piece from said port unit.

6. The port catheter as claimed in claim 1, wherein said base part includes at least one securement element configured to be inserted into the tissue for the securement of said port catheter to the tissue of the human or animal body.

7. The port catheter as claimed in claim 1, wherein said port unit includes a diaphragm arranged to be pierced by an injection needle for the supply of the fluid into said interior chamber.

8. The port catheter as claimed in claim 1, wherein said flexible tube is connected to said port unit at a factory.

9. The port catheter as claimed in claim 1, wherein said flexible tube is configured to remain connected to said port unit when said grip piece is removed from said port unit.

* * * * *